(12) United States Patent
Craig et al.

(10) Patent No.: US 7,976,259 B2
(45) Date of Patent: Jul. 12, 2011

(54) SYSTEM FOR FEEDING BIOMASS INTO A PRESSURIZED VESSEL

(76) Inventors: Joe David Craig, Tahoka, TX (US); Joe Don Nevill, Tahoka, TX (US); Lyle Allen Craig, Post, TX (US)

( * ) Notice: Subject to any disclaimer, the term of this patent is extended or adjusted under 35 U.S.C. 154(b) by 0 days.

(21) Appl. No.: 12/907,258

(22) Filed: Oct. 19, 2010

(65) Prior Publication Data
US 2011/0033268 A1   Feb. 10, 2011

Related U.S. Application Data

(63) Continuation-in-part of application No. 12/173,494, filed on Jul. 15, 2008, now abandoned.

(60) Provisional application No. 60/949,911, filed on Jul. 16, 2007, provisional application No. 60/949,920, filed on Jul. 16, 2007, provisional application No. 60/949,968, filed on Jul. 16, 2007, provisional application No. 60/949,957, filed on Jul. 16, 2007, provisional application No. 60/949,977, filed on Jul. 16, 2007, provisional application No. 60/949,982, filed on Jul. 16, 2007, provisional application No. 60/949,990, filed on Jul. 16, 2007, provisional application No. 60/949,917, filed on Jul. 16, 2007.

(51) Int. Cl.
*B65G 53/48* (2006.01)

(52) U.S. Cl. ......... 414/218; 198/660; 198/661; 198/676

(58) Field of Classification Search ............ 198/660, 198/661, 676; 414/218
See application file for complete search history.

(56) References Cited

U.S. PATENT DOCUMENTS

| | | | | |
|---|---|---|---|---|
| 1,959,864 A | * | 5/1934 | Hartley | 406/56 |
| 2,184,248 A | * | 12/1939 | Bonotto | 422/273 |
| 2,321,015 A | * | 6/1943 | Davis | 34/428 |
| 2,376,139 A | * | 5/1945 | Hemminger | 208/120.01 |
| 2,456,124 A | * | 12/1948 | Hoffman | 62/63 |
| 2,467,805 A | * | 4/1949 | Bressler | 122/4 R |
| 3,341,280 A | * | 9/1967 | Eolkin | 422/31 |
| 3,351,030 A | * | 11/1967 | Albertson et al. | 110/221 |
| RE26,908 E | * | 6/1970 | Alberson et al. | 110/245 |
| 3,756,434 A | * | 9/1973 | Teske | 414/218 |
| 3,841,465 A | * | 10/1974 | Miller et al. | 241/247 |
| 3,865,053 A | * | 2/1975 | Kolze et al. | 110/186 |
| 4,274,786 A | * | 6/1981 | Svensson et al. | 414/218 |
| 4,386,695 A | * | 6/1983 | Olson | 198/661 |
| 4,401,402 A | * | 8/1983 | Casperson | 414/218 |
| 4,466,809 A | * | 8/1984 | Kissel et al. | 48/197 R |
| 4,528,098 A | * | 7/1985 | Treyssac et al. | 210/414 |
| 4,553,285 A | * | 11/1985 | Sachs et al. | 110/223 |

(Continued)

*Primary Examiner* — Joe Dillon, Jr.
(74) *Attorney, Agent, or Firm* — Gagnon, Peacock, Shanklin & Vereake, P.C.; Aaron P. Peacock

(57) ABSTRACT

The present disclosure provides for a system for feeding biomass into a pressured vessel, the system includes a screw-feeding housing, a drive motor, a rotary airlock, a first conveyor screw, a second conveyor screw, a barrel, a low friction liner attached to a substantial portion of the inside surface of the barrel, a pressure sensor positioned within the screw-feeding housing for monitoring backpressure, a compression disk, an actuator, a function controller which controls the pressure sensor, the drive motor and the actuator, and a control loop which comprises the function controller, the actuator, the drive motor, and the pressure sensor for monitoring backpressure within the screw-feeding housing and for controlling and adjusting the force applied by the actuator to the compression disk and the torque applied by the drive motor to the first conveyor screw, thereby effectuating an effectively sealed biomass plug.

13 Claims, 2 Drawing Sheets

U.S. PATENT DOCUMENTS

| | | | |
|---|---|---|---|
| 4,702,177 A * | 10/1987 | Narisoko et al. | 110/110 |
| 4,738,687 A * | 4/1988 | Smieskol et al. | 48/197 R |
| 4,881,862 A * | 11/1989 | Dick | 414/218 |
| 5,052,874 A * | 10/1991 | Johanson | 414/326 |
| 5,088,422 A * | 2/1992 | Koenig | 110/173 R |
| 5,337,658 A * | 8/1994 | Bruke | 100/127 |
| 5,388,537 A * | 2/1995 | Larson et al. | 110/346 |
| 5,555,823 A * | 9/1996 | Davenport | 110/346 |
| 5,615,987 A * | 4/1997 | Weist | 414/218 |
| 5,996,770 A * | 12/1999 | Kjellqvist | 198/672 |
| 6,312,206 B1 * | 11/2001 | Pylate et al. | 414/345 |
| 6,976,575 B2 * | 12/2005 | Koch et al. | 198/657 |
| 7,153,077 B2 * | 12/2006 | Warner | 414/398 |
| 7,314,538 B2 * | 1/2008 | Lashofer et al. | 162/52 |
| 7,600,960 B2 * | 10/2009 | Christensen et al. | 414/805 |

\* cited by examiner

SYSTEM FOR FEEDING BIOMASS INTO A PRESSURIZED VESSEL

CROSS-REFERENCE TO RELATED APPLICATIONS

This application is a continuation-in-part of application Ser. No. 12/173,494 now abandoned, filed Jul. 15, 2008, which claims benefit of application Ser. No. 60/949,911, filed Jul. 16, 2007, application Ser. No. 60/949,920, file Jul. 16, 2007, application Ser. No. 60/949,968, filed Jul. 16, 2007, application Ser. No. 60/949,957, filed Jul. 16, 2007, application Ser. No. 60/949,977, filed Jul. 16, 2007, application Ser. No. 60/949,982, filed Jul. 16, 2007, application Ser. No. 60/949,990, filed Jul. 16, 2007, application Ser. No. 60/949,917, filed Jul. 16, 2007, the entire contents of which are incorporated herein by reference.

DETAILED DESCRIPTION

Figure 1:
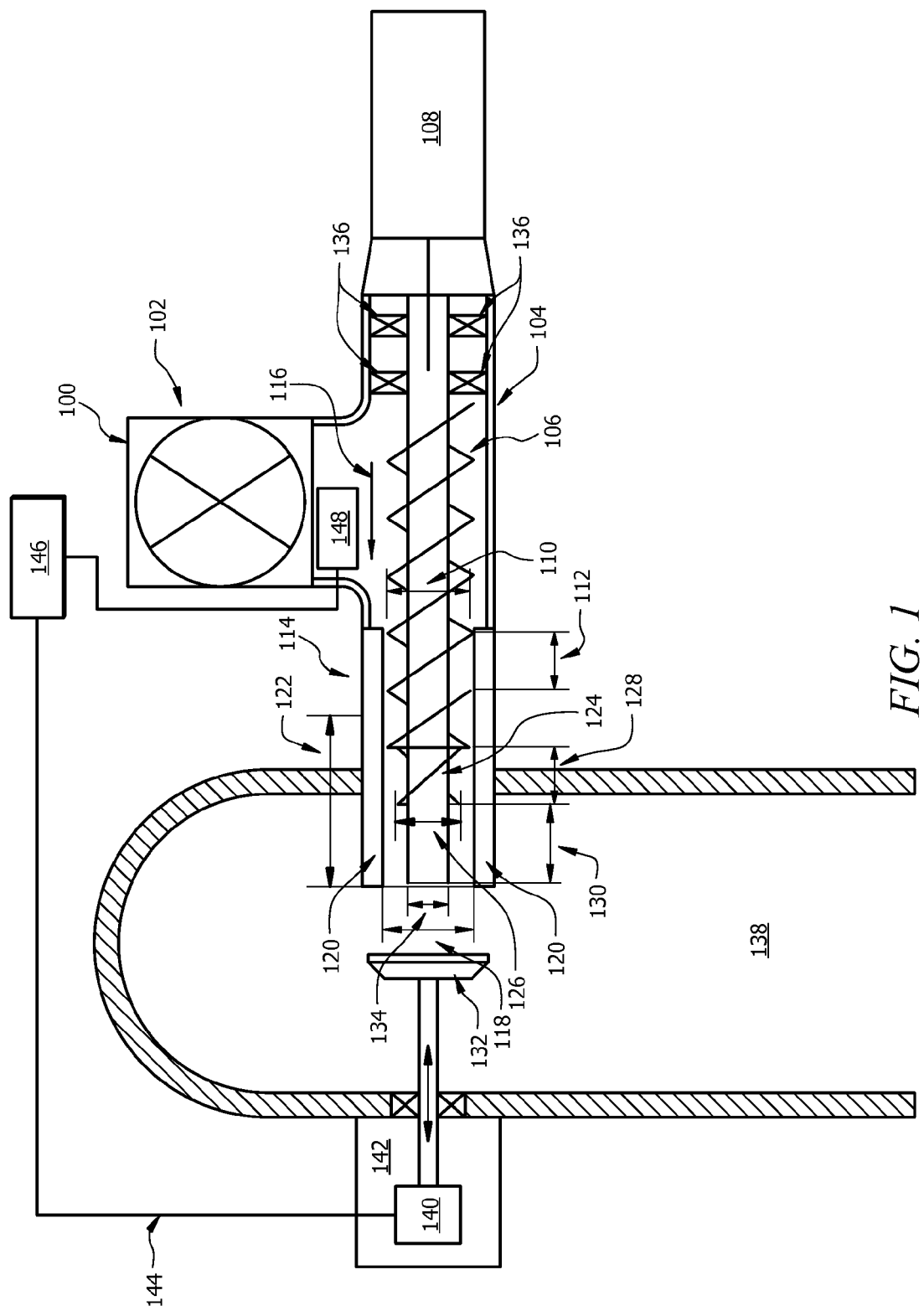
FIG. 1 is a side view of a screw-feeding device comprising an embodiment of the present invention.

Embodiments of the present invention provide for an improved system, method and apparatus for feeding biomass into a pressurized vessel. It is understood, however, that the following disclosure provides many different embodiments, or examples, for implementing different features of the invention. Specific examples of components, signals, messages, protocols, and arrangements are described below to simplify the present disclosure. Theses are merely examples and are not intended to limit the invention from that described in the claims. Well-known elements are presented without detailed description in order not to obscure the present invention with unnecessary detail. Details unnecessary to obtain a complete understanding of the present invention have been omitted inasmuch as such details are within the skills of persons of ordinary skill in the relevant art. Details regarding control circuitry described herein are omitted; as such, control circuits are within the skills of persons of ordinary skill in the relevant art.

New supplies of energy have been a major concern in today's society. With the increasing costs of fuel, and volatile situation in the Middle East, alternative supplies of energy have become more important to every major society in the world. In addition, efficient use of waste products has become a mandate from a waste conscious society, a society such as the United States. Agricultural waste products and other cellulosic waste material such as wood waste, also known as biomass, are reusable natural resources which can be utilized as a source of energy. Biomass can be converted into valuable gases through a process of gasification. A basic biomass gasification process has been in existence for many years and generally has been performed at pressures ranging from just below to just above atmospheric pressure. The gases produced during the gasification process can be utilized in heat production or to fuel reciprocating engines. It is, however, beneficial to gasify the biomass at pressures over two atmospheres. Gasifying biomass under pressure has many benefits. Increased efficiency is one such benefit. By eliminating the step of recompressing gas that is utilized in a pressurized process or system, greater efficiency is realized. For example, the produced gases from the biomass can feed various processes that operate under pressure without the need for recompression. Not only does gasifying biomass under pressure increase efficiency, but it increases simplicity. For example, fueling the high pressure combustion chamber of a gas turbine engine and feeding the gases to chemical processes operating under pressure can be performed in a more simplified manner.

Biomass is becoming a much more important feedstock for many chemical processes including gasification. A major impediment to the commercialization of certain biomass conversion processes is the economical injection of biomass into a pressurized vessel.

One embodiment of the present invention comprises a screw-feeding device and system for economically injecting biomass into vessels with pressures greater than one atmosphere. Biomass is defined herein as, but not limited to, cellulose fibers with varying amounts of lignin content. Such biomass material is also referred to as lignocellulosic, and includes materials ranging from high density wood to pure cotton fibers. Other examples of biomass material are sugarcane bagasse, straws, grasses, corn stover, rice hulls, nut shells, orchard prunings, animal manure, cotton gin trash, refuse derived fuels and other similar materials.

FIG. 1 depicts a screw-feeding device and system that is designed to convey biomass at atmospheric pressure into a vessel with a pressure greater than one atmosphere. Biomass is dropped into the inlet port 100 of a rotary airlock value 102. The rotary airlock valve 102 attaches to a screw-feeding housing 104 and transfers the biomass material from the inlet port 100 through the outlet port of the rotary airlock valve into the interior of the screw-feeding housing 104. The screw-feeding housing 104 comprises a first conveyor screw 106 which is rotated by a drive motor 108. Thrust bearings 136 assist in managing thrust that is exerted onto the first conveyor screw 106. In one embodiment as depicted in FIG. 1, the first conveyor screw 106 is double-flighted with a diameter 110 and a one-half pitch 112, and conveys the biomass material horizontally into a barrel 114 as shown by arrow 116. The barrel 114 has a constant inside diameter 118. A majority of the inside surface of the barrel 114 has a very low friction liner 120 or coating that is wear resistant. The length 122 of the low friction liner 120 is shorter than the barrel 114. Attached to and/or integral with the end of the first conveyor screw 106 is a double-flighted second conveyor screw 124 with a diameter 126 and a one-half pitch 128. The end of the second conveyor screw 124 is a bare shaft of a diameter 134 and a length 130.

Figure 2:
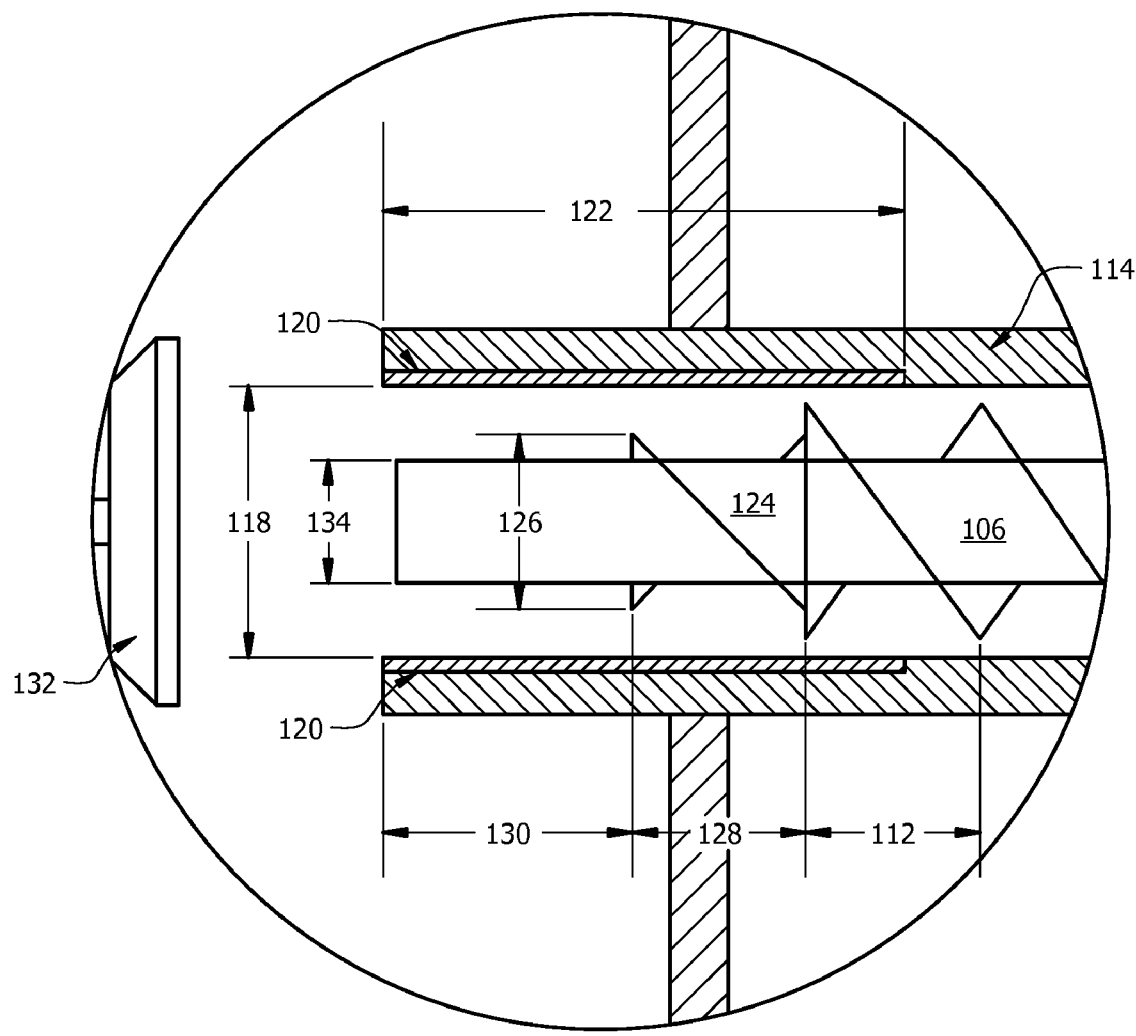
FIG. 2 is an enhancement of the side view of a portion of FIG. 1.

FIG. 2 depicts a magnification of the barrel 114, the low friction liner 120, the first conveyor screw 106 and a compression disk 132, as well as their respective diameters, lengths and pitches.

Referring back to FIG. 1, the first conveyor screw 106 pushes the biomass into a high pressure vessel 138. However, the compression disk 132 forces a backpressure onto the biomass exiting the barrel 114. This backpressure helps create a biomass plug. Specifically, the compression disk 132 translates horizontally while being acted upon by an actuator 140 that is within a housing 142. The actuator 140 imposes a force on the compression disk 132 which, in turn, causes a force onto the biomass in a direction opposite the exiting biomass, thereby controlling the density and size of the biomass plug. The plug formed by the compressed biomass is a pressure resistant seal at the outlet end of the barrel 114.

In the embodiment depicted in FIG. 1, the speed of rotation of the first conveyor screw 106 controls the maximum capacity of the device. However, the mass flow rate of biomass entering the inlet port 100 controls the actual rate of mass flow of the device. Moreover, the plug forms a doughnut-like shape because the outlet of the barrel 114 and the end of the second conveyor screw 124, which are positioned in the high pressure vessel 138, both are defined by circular structures. Additionally, the density of the plug can be controlled by the amount of force imposed by the actuator 140 onto the compression disk 132. Furthermore, the amount of torque required to rotate the first screw 106 can be controlled by the force exerted by the compression disk 132 onto the exiting biomass. The torque rating of the drive motor 108 determines the amount of torque that can be applied to rotate the first conveyor screw 106.

The system manages and controls the amount of force applied by the actuator 140 and the drive motor 108 as well as the rate of biomass entering the inlet port 100, thereby managing and controlling the density and size of the plug. Moreover, the physical characteristics of the biomass including the amount of moisture present therein also contribute to the density and size of the plug.

To effectively manage and control the size and density of the plug via the actuator 140 and the drive motor 108, a control loop 144 can be implemented to monitor and control backpressure. A pressure sensor 148 can monitor the backpressure and relay such information to a function controller 146 which adjusts the actuator 140 and drive motor 108 accordingly. As a result, the force applied by the actuator 140 is a function of the backpressure. The detection and monitoring of the backpressure by the pressure sensor 148 requires the utilization of the rotary airlock valve 102 or similar device which ensures that the interior of the screw-feeding housing 104 is kept substantially airtight during system operations, thereby substantially impeding airflow between the interior of the screw-feeding housing 104 and the inlet port 100. Consequently, when backpressure is detected via the pressure sensor 148, the system can adjust itself to effectuate an effectively sealed plug.

Persons of ordinary skill in the relevant art will appreciate that embodiments of the present invention can include a variety of differing measurements and dimensions for the various parts and components. For example, the drive motor 108 can be a 10 horsepower gear motor. The first conveyor screw 106 can be double flighted and have a diameter 110 of four and one-half inches and one-half pitch 112 of three inches. The diameter 118 of the barrel 114 can be five inches. The length of the low friction liner 120 can be nine inches. The second conveyor screw 124 can have a diameter 126 of three and one-half inches, a one-half pitch of three inches, a bare shaft diameter 126 of two and three-eighths inches, and a length 130 of four inches.

Additionally, persons of ordinary skill in the relevant art will appreciate that embodiments of the present invention can include a variety of differing materials for the various parts and components. For example, the high pressure vessel 138 and the first conveyor screw 106 can be comprised of material such as stainless steel, ceramic or other like material. The low friction liner 120 can be comprised of replaceable stainless steel, steel, ceramic, or a ceramic-coated based material. It is recommended that for greater wear resistance, wear-resistant materials should be used for the first conveyor screw 106, conveyor 124, and the barrel 114.

The embodiments of the present invention apply to conveyor screws, regardless of type, function or properties, drive motors, regardless of type, function or properties, barrels, regardless of type, function or properties, friction liners, regardless of type, function or properties, screw conveyors, regardless of type, function or properties, compression disks, regardless of type, function or properties, thrust bearings, regardless of type, function or properties, high pressure vessels, regardless of type, function, or properties, actuators, regardless of type, function or properties, pressure sensors, regardless or type, function or properties, function controllers, regardless of type, function or properties, and rotary airlock valves, regardless of type, function or properties.

Although the many embodiments of the invention have been illustrated in the accompanying Drawings and described in the foregoing Detailed Description, it should be understood that the present invention is not limited to the embodiments disclosed, but is capable of numerous rearrangements, modifications, and substitutions of parts and elements without departing from the spirit of the invention.

What is claimed is:

1. A system for feeding biomass into a pressured vessel, the system comprising:
    a screw-feeding housing;
    a drive motor attached to the screw-feeding housing;
    a rotary airlock valve attached to the screw-feeding housing, wherein the rotary airlock valve has an inlet port for receiving biomass material and an outlet port for disposing biomass material into the interior of the screw-feeding housing and wherein the rotary airlock valve substantially impedes airflow between the interior of the screw-feeding housing and the inlet port;
    a first conveyor screw disposed within the screw-feeding housing for receiving biomass material from the outlet port of the rotary airlock valve and conveying biomass material through the screw-feeding housing, wherein the first conveyor screw is double flighted and has a diameter;
    a second conveyor screw disposed within the screw-feeding housing and attached to the first conveyor screw, wherein the second conveyor screw has a diameter smaller than the diameter of the first conveyor screw and wherein the second conveyor screw has a bare shaft;
    a barrel disposed within the screw-feeding housing, wherein the second conveyor screw and a portion of the first conveyor screw are disposed within the barrel and wherein the barrel receives biomass material from the first conveyor screw and the second conveyor screw;
    a low friction liner attached to a substantial portion of the inside surface of the barrel, wherein the length of the low friction liner is shorter than the length of the barrel;
    a pressure sensor positioned within the screw-feeding housing for monitoring backpressure;
    a compression disk position at the outlet of the barrel for compressing biomass material before the material falls from the outlet of the barrel into the pressurized vessel, thereby forming a biomass plug at the outlet of the barrel;
    an actuator connected to the compression disk, wherein the actuator imposes a translational force upon the compression disk;
    a function controller which controls the pressure sensor, the drive motor and the actuator; and
    a control loop which comprises the function controller, the actuator, the drive motor, and the pressure sensor for monitoring backpressure within the screw-feeding housing and for controlling and adjusting the force applied by the actuator to the compression disk and the torque applied by the drive motor to the first conveyor screw, thereby effectuating an effectively sealed biomass plug.

2. The system of claim 1 wherein the drive motor is a 10 horsepower gear motor.

3. The system of claim 2 wherein the first conveyor screw has a diameter of four and one-half inches.

4. The system of claim 3 wherein the first conveyor screw has a one-half pitch of three inches.

5. The system of claim 4 wherein the barrel has a diameter of five inches.

6. The system of claim 5 wherein low friction liner has a length of nine inches.

7. The system of claim 6 wherein the second conveyor screw has a diameter of three and one-half inches.

8. The system of claim 7 wherein the second conveyor screw has a one-half pitch of three inches.

9. The system of claim 8 wherein the second conveyor screw has a diameter of two and three-eighths inches.

10. The system of claim 9 wherein the second conveyor screw has a length of four inches.

11. The system of claim 10 wherein the first conveyor screw is comprised of stainless steel.

12. The system of claim 11 wherein the low friction liner is comprised of stainless steel.

13. The system of claim 11 wherein the low friction liner is comprised of ceramic.

* * * * *